(12) United States Patent
Cooper et al.

(10) Patent No.: US 10,835,320 B2
(45) Date of Patent: Nov. 17, 2020

(54) SYSTEMS AND METHODS FOR A DUAL-CONTROL SURGICAL INSTRUMENT

(71) Applicant: INTUITIVE SURGICAL OPERATIONS, INC., Sunnyvale, CA (US)

(72) Inventors: Thomas G. Cooper, Menlo Park, CA (US); David Q. Larkin, Menlo Park, CA (US); Paul E. Lilagan, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 270 days.

(21) Appl. No.: 15/806,920

(22) Filed: Nov. 8, 2017

(65) Prior Publication Data
US 2018/0064493 A1    Mar. 8, 2018

Related U.S. Application Data

(62) Division of application No. 14/079,142, filed on Nov. 13, 2013, now Pat. No. 9,820,816.
(Continued)

(51) Int. Cl.
*A61B 17/29* (2006.01)
*A61B 34/35* (2016.01)
(Continued)

(52) U.S. Cl.
CPC .............. *A61B 34/10* (2016.02); *A61B 34/30* (2016.02); *A61B 34/35* (2016.02);
(Continued)

(58) Field of Classification Search
CPC ......... A61B 17/28; A61B 17/29; A61B 34/30; A61B 34/32; A61B 34/35; A61B 34/37; A61B 34/70; A61B 34/74
See application file for complete search history.

(56) References Cited

U.S. PATENT DOCUMENTS

| 5,304,203 A | 4/1994 | El-Mallawany et al. |
| 5,370,659 A * | 12/1994 | Sakashita ............... A61B 17/29 |
| | | 600/564 |

(Continued)

FOREIGN PATENT DOCUMENTS

| CN | 101925333 A | 12/2010 |
| EP | 1570789 A2 | 9/2005 |

(Continued)

OTHER PUBLICATIONS

Extended European Search Report for Application No. 13854350.9, dated Jun. 17, 2016, 9 pages.
(Continued)

*Primary Examiner* — Kathleen S Holwerda
(74) *Attorney, Agent, or Firm* — Haynes and Boone, LLP.

(57) ABSTRACT

A surgical system comprises an instrument and a teleoperated instrument operation system. The instrument comprises a drive member having an end effector coupled to the distal end and a ratchet assembly coupled to the proximal end. The ratchet assembly includes a pin, a gear, and a spring-loaded button. A lever is coupled to and configured to pivot relative to the ratchet assembly to engage the spring-loaded button to disengage the pin from the gear. The lever in a first position places the ratchet assembly in a gripping position in which the end effector grips a surgical accessory. The lever in a second position places the ratchet assembly in a release position in which the end effector releases the surgical accessory. The lever is movable while compressing the spring-loaded button. The teleoperated instrument operation system comprises a capture mechanism configured to move the lever between the first and second positions.

9 Claims, 12 Drawing Sheets

Related U.S. Application Data

(60) Provisional application No. 61/726,415, filed on Nov. 14, 2012.

(51) Int. Cl.
*A61B 34/10* (2016.01)
*A61B 34/30* (2016.01)
*A61B 17/00* (2006.01)

(52) U.S. Cl.
CPC ............. *A61B 2017/00314* (2013.01); *A61B 2017/00398* (2013.01); *A61B 2017/00407* (2013.01); *A61B 2017/00725* (2013.01); *A61B 2017/2902* (2013.01); *A61B 2017/292* (2013.01); *A61B 2017/2946* (2013.01); *Y10S 901/31* (2013.01)

(56) References Cited

U.S. PATENT DOCUMENTS

| | | |
|---|---|---|
| 5,622,090 A | 4/1997 | Marks |
| 5,626,608 A * | 5/1997 | Cuny ................ A61B 17/2909 600/131 |
| 5,792,135 A | 8/1998 | Madhani et al. |
| 6,331,181 B1 | 12/2001 | Tierney et al. |
| 6,424,885 B1 | 7/2002 | Niemeyer et al. |
| 6,491,701 B2 | 12/2002 | Tierney et al. |
| 6,645,196 B1 | 11/2003 | Nixon et al. |
| 6,770,081 B1 | 8/2004 | Cooper et al. |
| 6,817,974 B2 | 11/2004 | Cooper et al. |
| 7,942,868 B2 | 5/2011 | Cooper |
| 7,996,110 B2 | 8/2011 | Lipow et al. |
| 8,485,576 B2 | 7/2013 | Melville et al. |
| 2005/0021078 A1 | 1/2005 | Vleugels et al. |
| 2005/0059960 A1 | 3/2005 | Simaan et al. |
| 2006/0161136 A1 | 7/2006 | Anderson et al. |
| 2007/0005002 A1 | 1/2007 | Millman et al. |
| 2007/0016174 A1 | 1/2007 | Millman et al. |
| 2007/0100254 A1 | 5/2007 | Murakami et al. |
| 2007/0137371 A1 | 6/2007 | Devengenzo et al. |
| 2007/0185486 A1 | 8/2007 | Hauck et al. |
| 2008/0065105 A1 | 3/2008 | Larkin et al. |
| 2008/0228196 A1 | 9/2008 | Wang et al. |
| 2009/0024142 A1 | 1/2009 | Ruiz Morales |
| 2009/0036740 A1 | 2/2009 | Finlay |
| 2009/0314122 A1 | 12/2009 | Youn et al. |
| 2011/0004225 A1 | 1/2011 | Choi et al. |
| 2011/0015484 A1 * | 1/2011 | Alvarez ................ A61B 1/307 600/109 |
| 2011/0277580 A1 | 11/2011 | Cooper et al. |
| 2011/0277775 A1 | 11/2011 | Holop et al. |
| 2012/0065470 A1 | 3/2012 | Olds et al. |

FOREIGN PATENT DOCUMENTS

| | | |
|---|---|---|
| EP | 1707153 A1 | 10/2006 |
| EP | 1815950 A1 | 8/2007 |
| EP | 1864615 A2 | 12/2007 |
| EP | 1970014 A1 | 9/2008 |
| WO | WO-2006016390 A1 | 2/2006 |
| WO | WO-2007041094 A1 | 4/2007 |
| WO | WO-2007146987 A2 | 12/2007 |
| WO | WO-2010062380 A3 | 8/2010 |
| WO | WO-2011002215 A2 | 1/2011 |
| WO | WO-2011008922 A2 | 1/2011 |
| WO | WO-2011060139 A2 | 5/2011 |

OTHER PUBLICATIONS

International Search Report and Written Opinion for Application No. PCT/US2013/069856, dated Feb. 11, 2014, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR A DUAL-CONTROL SURGICAL INSTRUMENT

CROSS-REFERENCE TO RELATED APPLICATIONS

This application is a divisional application of U.S. application Ser. No. 14/079,142 filed Nov. 13, 2013 which claims the benefit of U.S. Provisional Application 61/726,415 filed Nov. 14, 2012, all of which are incorporated by reference herein in their entirety.

FIELD

The present disclosure is directed to surgical systems and methods for use in minimally invasive teleoperational surgery, and more particularly to systems and methods for implementing a dual-control surgical instrument.

BACKGROUND

Minimally invasive medical techniques are intended to reduce the amount of extraneous tissue that is damaged during diagnostic or surgical procedures, thereby reducing patient recovery time, discomfort, and deleterious side effects. Minimally invasive telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In telesurgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instrument's position, orientation, and articulation at the surgical site. The slave is an electro-mechanical assembly which includes a plurality of arms, joints, linkages, servo motors, etc. that are connected together to support and control the surgical instruments. In a surgical procedure, the surgical instruments (including an endoscope) may be introduced directly into an open surgical site or more typically through cannulas into a body cavity.

For minimally invasive surgical procedures, the surgical instruments, controlled by the surgical manipulator, may be introduced into the body cavity through a single surgical incision site or through multiple closely spaced incision sites on the patient's body. These minimally invasive procedures may present multiple challenges. For example, some procedures that require the manual introduction of surgical implements such as sutures, gauze, sponges, clamps, and needles, may require the use of separate instruments. A teleoperated instrument may be removed from the surgical manipulator and a manual instrument inserted into the patient to hand off a surgical accessory to another teleoperated instrument. The manual instrument is then removed so that the teleoperated instrument may be reintroduced. This type of hand off procedure is time consuming and requires the use of separate manual and teleoperated instruments. Improved systems and methods are needed to improve efficiency in procedures that involve the introduction of surgical implements, while maintaining safety and accuracy throughout the surgery.

SUMMARY

The embodiments of the invention are summarized by the claims that follow below.

In one embodiment, a method comprises receiving a surgical instrument into engagement with a grip actuator of a teleoperational activation system. The surgical instrument includes movable jaws, and the surgical instrument is received in a prearranged gripping configuration with the jaws gripping a surgical accessory. The method includes generating a first control signal for manipulating the surgical instrument while maintaining the surgical instrument in the prearranged gripping configuration. The method further includes generating a second control signal for manipulating the surgical instrument to move from the prearranged gripping configuration to a second configuration.

In another embodiment, a surgical system comprises an instrument body including an end effector sized to grip a surgical accessory and a dual-control instrument activation system coupled to the instrument body. The dual-control instrument activation system includes a lever operable, in response to manual manipulation, to move between a first position in which the end effector is in an open configuration for receipt of a surgical accessory and a second position in which the end effector is in a closed gripping configuration. The surgical system further comprises an instrument operation system responsive to teleoperational signals. The instrument operation system includes a lever capture mechanism to engage the lever in the second position to maintain the closed gripping configuration. The lever capture mechanism also moves the lever to the first position.

In another embodiment, a surgical system comprises an instrument including an end effector sized to grip a surgical accessory. The surgical system also comprises a dual-control instrument activation system to control the end effector. The dual-control instrument activation system includes a ratchet assembly coupled to a lever. In response to manual manipulation, the lever moves the ratchet assembly to a gripping position in which the end effector is arranged to grip the surgical accessory. The surgical system also comprises an instrument operation system that is responsive to teleoperational signals. The instrument operation system includes a lever capture mechanism to engage the lever to move the ratchet assembly to a release position in which the end effector is arranged to release the surgical accessory.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Figure 1:
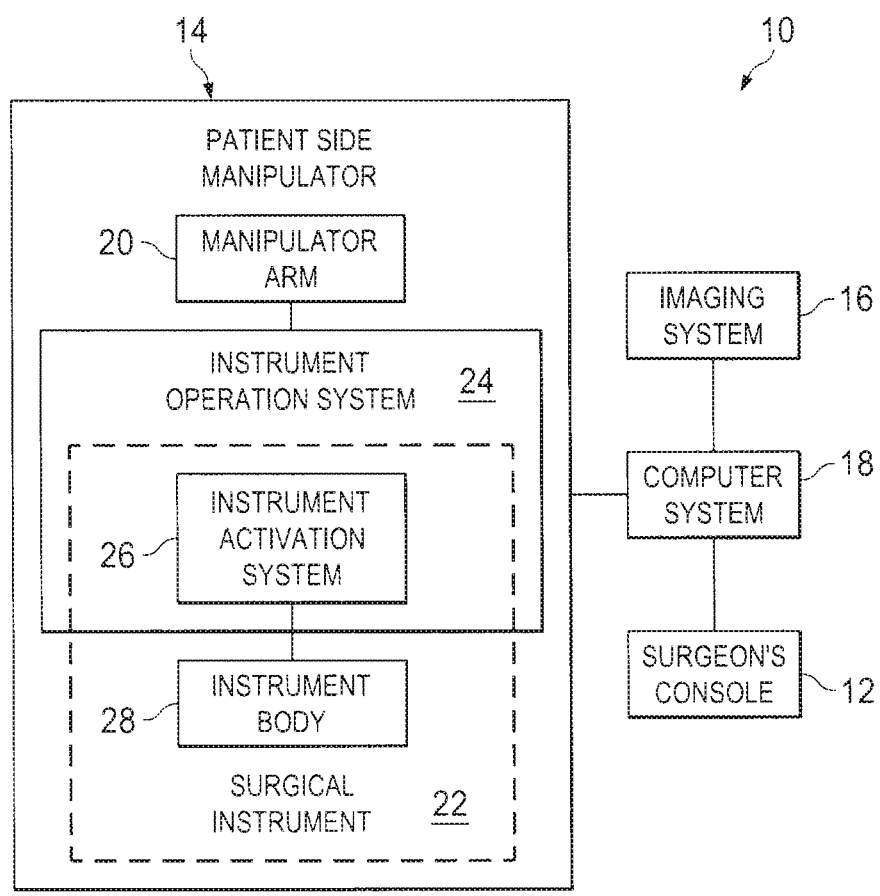
FIG. 1 illustrates a schematic view of a teleoperated surgical system according to one embodiment of the present disclosure.

FIG. 1 illustrates a schematic view of a teleoperated surgical system 10 according to one embodiment of the present disclosure. The system 10 includes a master surgeon console or workstation 12 for inputting a surgical procedure and a patient side cart (or "PSC") 14 for moving surgical instruments, via teleoperational control, at a surgical site within a patient. The teleoperated surgical system 10 is used to perform minimally invasive teleoperated surgery. One example of a teleoperated surgical system that can be used to implement the systems and techniques described in this disclosure is a da Vinci® Surgical System commercialized by Intuitive Surgical, Inc. of Sunnyvale, California. Those skilled in the art will understand that the inventive aspects disclosed herein may be embodied and implemented in various ways, including teleoperated and non-teleoperated embodiments and implementations. Implementations on da Vinci® Surgical Systems are merely exemplary and are not to be considered as limiting the scope of the inventive aspects disclosed herein. Further details of these exemplary teleoperated surgical systems are provided, for example, in pending U.S. patent application Ser. No. 12/855,461, the full disclosure of which is incorporated herein by reference.

The system 10 is used by a system operator, generally a surgeon, who performs a minimally invasive surgical procedure on a patient. The system operator sees images captured by an image system 16 and presented for viewing at the master console 12. In response to the surgeon's input commands, a computer system 18 effects servomechanical movement of surgical instruments coupled to the teleoperated patient-side manipulator system 14 (a cart-based system in this example).

Computer system 18 will typically include data processing hardware and software, with the software typically comprising machine-readable code. The machine-readable code will embody software programming instructions to implement some or all of the methods described herein. While computer system 18 is shown as a single block in the simplified schematic of FIG. 1, the system may comprise a number of data processing circuits (e.g., on the surgeon's console 12 and/or on the patient-side manipulator system 14), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the teleoperated systems described herein. In one embodiment, computer system 18 may support wireless communication protocols such as Bluetooth, IrDA, HomeRF, IEEE 802.11, DECT, and Wireless Telemetry.

The PSC 14 may be mobile (e.g., including wheels) or stationary. PSC 14 includes a manipulator arm 20 that effects movement of a surgical instrument 22 for manipulation of tissues. An instrument operation system 24 is coupled to the manipulator arm 20 and includes actuation components to control the movement of the surgical instrument 22. The instrument 22 includes a dual-control instrument activation system 26 and an instrument body 28. As will be described in greater detail below, the instrument body 28 may include a shaft and an end effector. The dual-control instrument activation system 26 functions as an actuating component of the instrument operation system 24 but is separable from other actuating components of the instrument operation system. When the surgical instrument 22 is decoupled from the instrument operation system 24, the dual-control instrument activation system 26 may be used to manually control the operation of the surgical instrument 22.

For example, a surgical assistant may decouple a gripping surgical instrument and dual-control instrument activation system 26 from the instrument operation system 24. The assistant may manually manipulate the dual-control instrument activation system 26 to cause the surgical instrument to grip a surgical accessory such as a needle or a clamp. The surgical assistant may then reconnect the dual-control instrument activation system 26 and surgical instrument, now gripping the surgical accessory, to the instrument operation system 24. The instrument operation system 24, via the dual-control instrument activation system 26, maintains the grip of the surgical instrument on the surgical accessory while the surgical instrument is moved into and within the surgical site. Thus, the dual-control instrument activation system 26 may be controlled by manual operator inputs and by teleoperational inputs.

The actuation components of the instrument operation system 24 may include a grip output controlling a gripping end effector, a joggle output controlling the side-to-side and up-down motion of the end effector, a wrist output controlling yaw and pitch motions of the end effector, and a roll output controlling a roll output of the end effector. Components for one or more of these actuations may be included in the dual-control instrument activation system 26.

Figure 2:
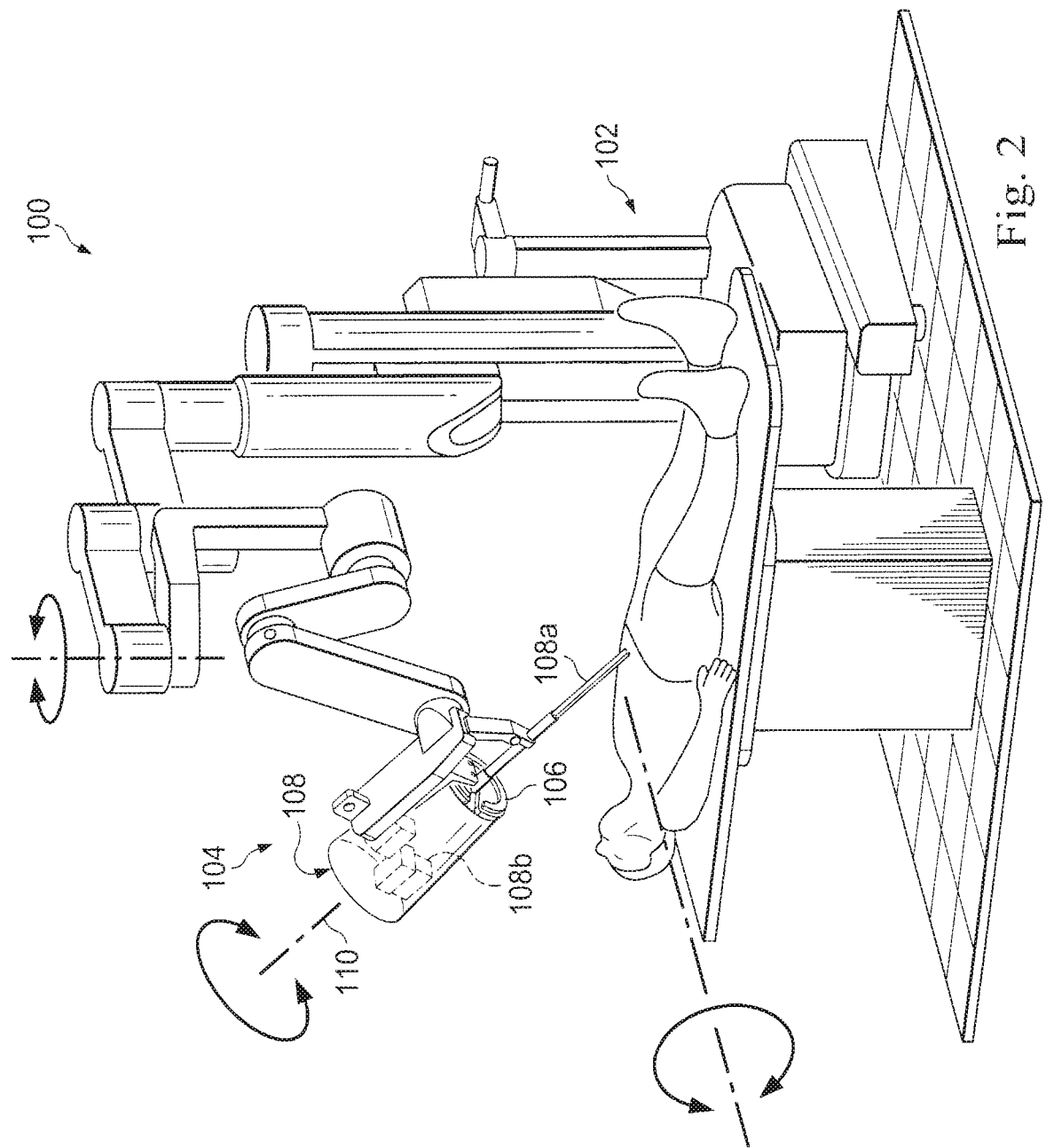
FIG. 2 illustrates a diagrammatic perspective view of a patient side manipulator according to one embodiment of the present disclosure.

The PSC may include all of the actuation components, including motors, the power sourced and control systems, that control the instrument. In alternative embodiments, some or all of the motors may be in the instrument with the PSC supplying the power and the control signals to the instrument. In still another alternative, the instrument may be battery powered with the PSC providing only control signals to the instrument FIG. 2 illustrates a diagrammatic perspective view of a PSC 100 according to an illustrative embodiment of the PSC 14 described above with reference to FIG. 1. In this embodiment, the PSC 100 includes a floor-mounted base 102. The base may be movable or fixed (e.g., to the floor, ceiling, wall, or other sufficiently rigid structure). Base 102 supports an arm assembly 104. The arm assembly 104 includes active joints and links for manipulator arm configuration and movement, instrument manipulation, and instrument insertion.

The arm assembly 104 includes a manipulator assembly disk or platform 106. An instrument cluster 108 is mounted to platform 106. The center of platform 106 is coincident with a manipulator assembly roll axis 110, as shown by the dashed line that extends through the center of manipulator platform 106. The instrument cluster 108 includes instrument shafts 108a mounted to instrument actuators 108b. Each instrument shaft 108a is mounted on a distal face of an instrument actuator 108b, in one embodiment.

Figure 3:
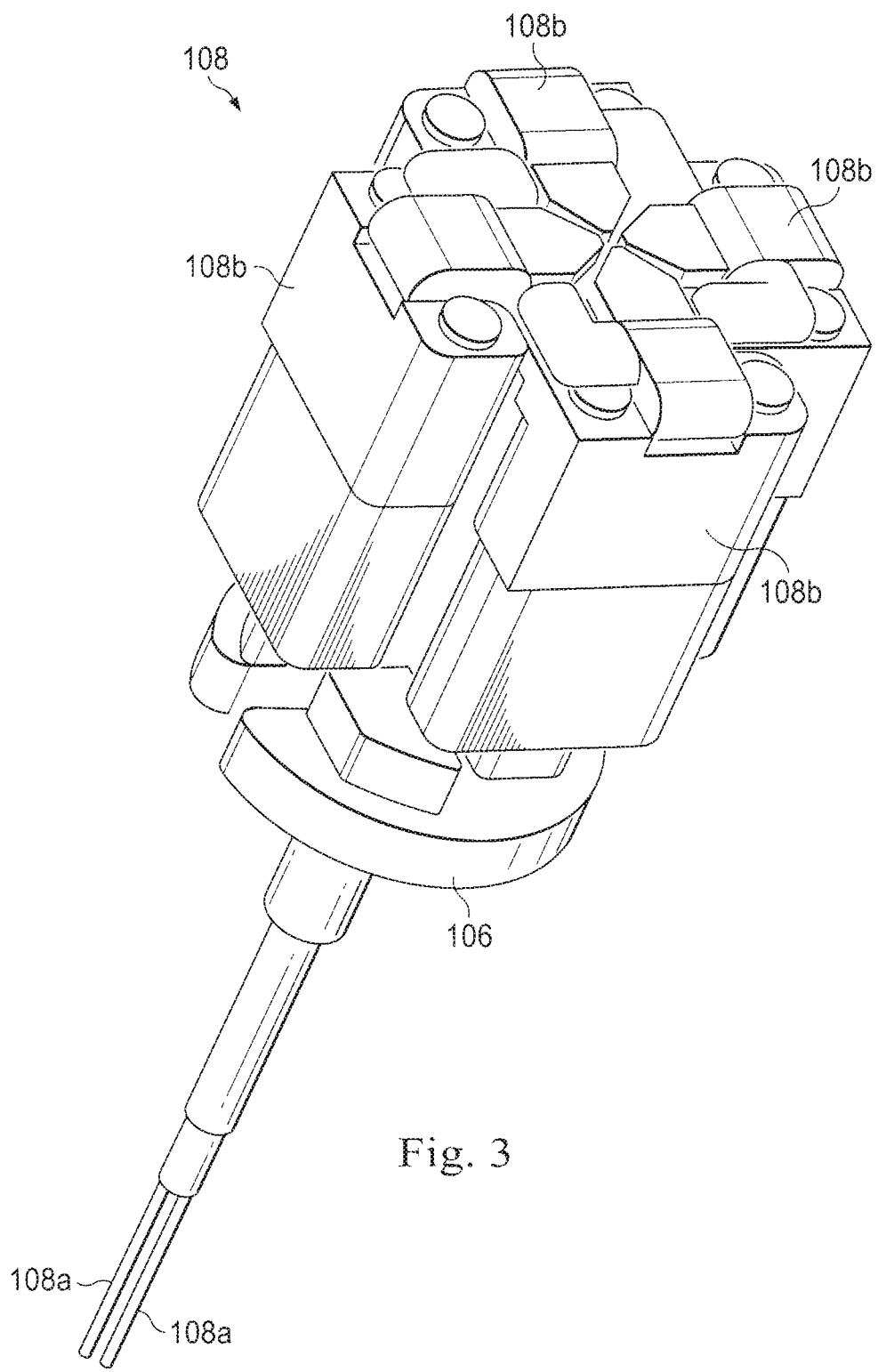
FIG. 3 illustrates a perspective view of a cluster of surgical instruments for use with the teleoperated surgical system of FIG. 2.

As shown in FIG. 3, instrument cluster 108 includes four instrument actuators 108b. Each instrument actuator 108b supports and actuates an associated surgical implement. For example, one instrument actuator 108b is configured to actuate a camera instrument, and three instrument actuators 108b are configured to actuate various other interchangeable surgical end effectors that perform surgical and/or diagnostic work at the surgical site. Articulated end effectors may include jaws, scissors, graspers, needle holders, microdissectors, staple appliers, tackers, suction irrigation tools, and clip appliers, that may be driven by wire links, eccentric cams, push-rods, or other mechanisms. In addition, the surgical instruments may comprise a non-articulated instrument, such as cutting blades, probes, irrigators, catheters or suction devices. Alternatively, the surgical tool may comprise an electrosurgical probe for ablating, resecting, cutting or coagulating tissue. Examples of applicable adaptors, tools or instruments, and accessories are described in U.S. Pat. Nos. 6,331,181, 6,491,701, and 6,770,081, the full disclosures of which (including disclosures incorporated by reference therein) are incorporated by reference herein for all purposes. Applicable surgical instruments are also commercially available from Intuitive Surgical, Inc. of Sunnyvale, Calif. More or fewer instrument actuators may be used. In some operational configurations, one or more actuators may not have an associated surgical instrument during some or all of a surgical procedure.

The instruments 108 are mounted so that shafts 108a are clustered around manipulator assembly roll axis 110. Each shaft 108a extends distally from the instrument's force transmission mechanism, and all shafts may extend through a single cannula placed at a port into the patient surgical site. Each instrument actuator 108b is movable to allow insertion and withdrawal of the surgical instrument(s).

Figure 4:
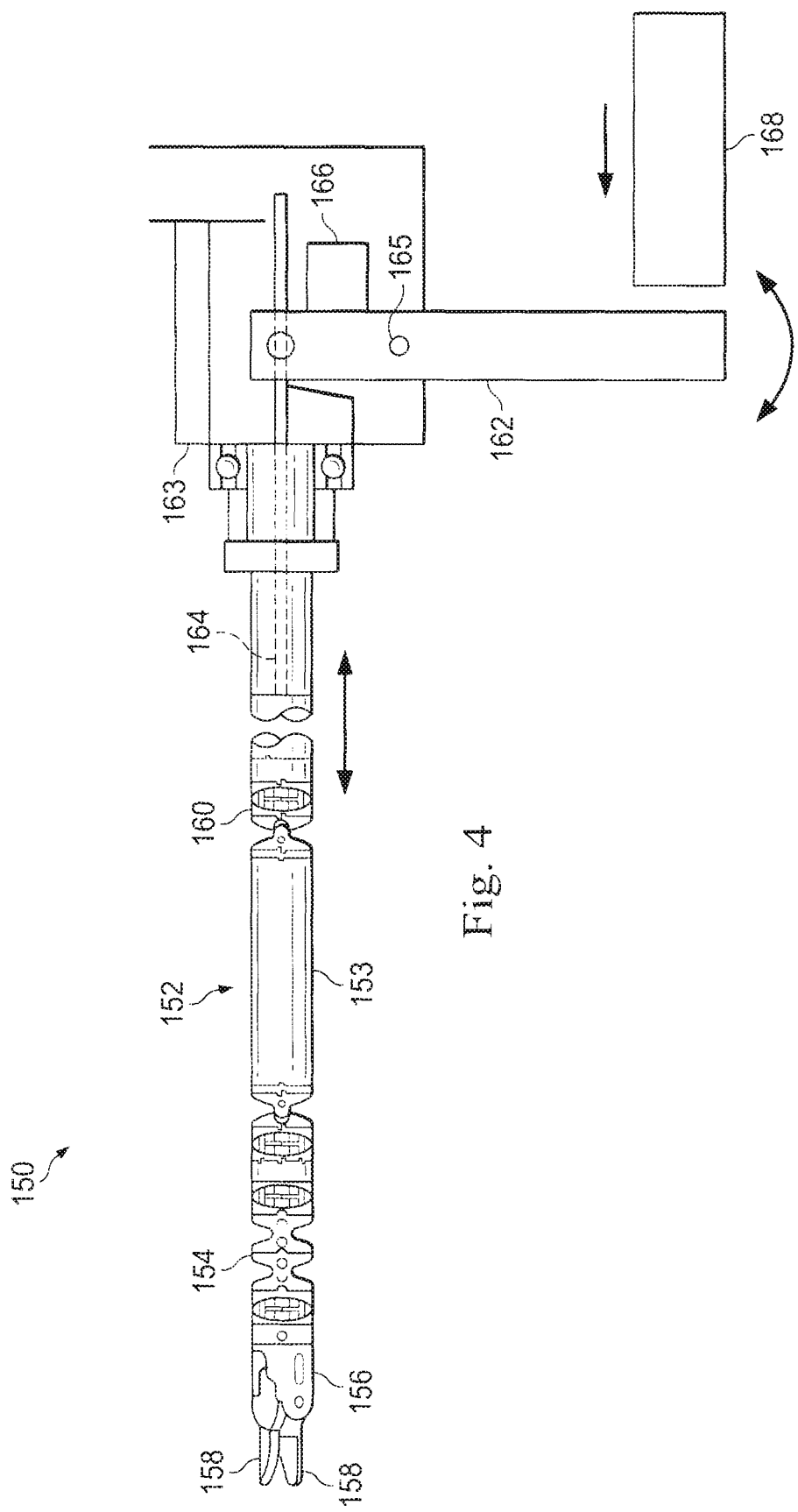
FIG. 4 is a partially schematic illustration of a dual-control surgical instrument according to an embodiment of this disclosure.

FIG. 4 is a partially schematic illustration of a dual-control surgical instrument 150 according to an embodiment of this disclosure. Instrument 150 is an illustrative embodiment of an instrument 22, 108 described above with reference to FIGS. 1 and 3, respectively. The dual-control surgical instrument 150 includes a parallel motion mechanism 152 with a tube 153 having joints at each end, coupled to a wrist joint 154, which is coupled to the end effector 156. In this embodiment, the end effector 156 includes jaws 158. In some aspects, the parallel motion mechanism 152 and wrist joint 154 function such that the position of a reference frame at the distal end of the mechanism may be changed with respect to a reference frame at the proximal end of the mechanism without changing the orientation of the distal reference frame. Details of an applicable parallel motion assembly including related joints of an applicable instrument are further disclosed in U.S. patent application Ser. No. 11/762,165 filed Jun. 13, 2007, disclosing "Minimally Invasive Surgical System" and U.S. Pat. No. 7,942,868 filed Jun. 13, 2007, disclosing "Surgical Instrument with Parallel Motion Mechanism," which are incorporated by reference herein in their entirety.

The parallel motion mechanism 152 is coupled to a distal end of a shaft 160. The proximal end of the shaft 160 is coupled to an instrument body 163. A lever 162 is coupled to the body 163 by a pivot joint 165. As will be described in other embodiments, the lever 162 may be manually or teleoperationally actuated. The lever 162 is coupled to a drive element 164. In this embodiment, the drive element is a single rod 164 which may be formed of nitinol, stainless steel, or another suitable medical-grade metal, ceramic, or polymer. Alternatively, the rod 164 may include more than one material. For example, a more flexible material may be used in areas that extend through the joints. In one embodiment, a distal portion of the rod may include a tungsten cable with an ethylene tetrafluoroethylene (ETFE) covering and a proximal portion formed of stainless steel. Optionally, a fluorinated ethylene propylene (FEP) covering may extend over all or a portion of the rod. The rod 164 may extend through the shaft 160 to couple with the end effector 156. In this embodiment, counter-clockwise rotation of the lever 162 about the pivot joint 165 advances the rod 164 linearly (i.e., moves the rod in the distal direction) to open the jaws of the end effector 156. Clockwise rotation of the lever 162 about the pivot joint 165 retracts the rod 164 linearly (i.e., moves the rod in the proximal direction) to close the jaws of the end effector 156. In an alternative embodiment, the rotation of the lever may have the opposite influence on the rod (i.e. counter-clockwise rotation retracts the rod and clockwise rotation advances the rod). In various embodiments, the rod may be configured such that advancement may either open or close the end effector. Likewise, the retraction may either open or close the end effector. The instrument 150 also includes a securing component 166 (e.g., one or more springs, a ratchet mechanism) which holds or biases the lever 162 in a position such that the jaws of the end effector 156 are held in a prearranged gripping position without a manual or teleoperated actuator providing a force to the lever. The lever 162 may be actuated by a force received by an actuator 168. The force provided by the actuator 168 may overcome the securing force provided by the securing component 166 to move the lever 162 and thus move the end effector from the prearranged closed gripping configuration to a released open configuration.

Figure 5:
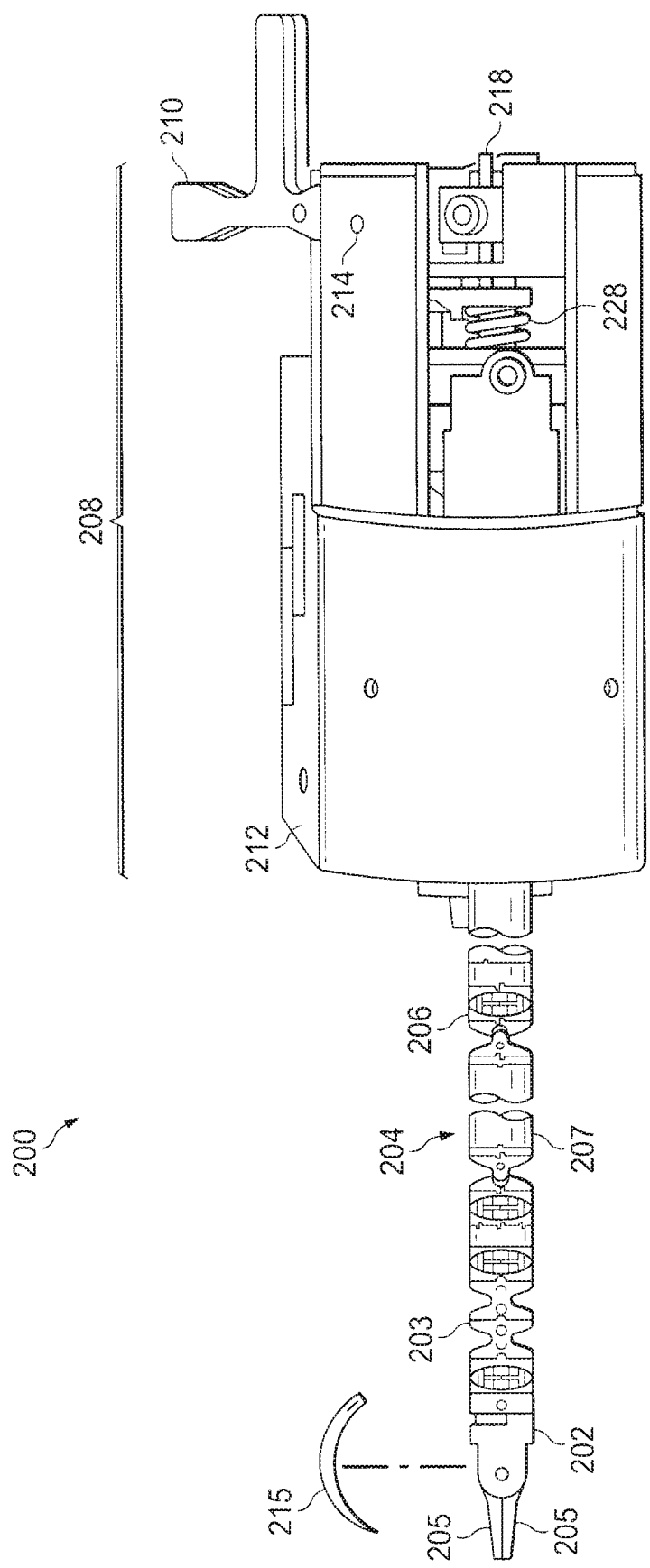
FIG. 5 illustrates a side view of a dual-control surgical instrument with an end effector in a closed position according to one embodiment of the present disclosure.

FIG. 5. illustrates a side view of a dual-control surgical instrument 200 with an end effector 202 in a closed position. Instrument 200 is an illustrative embodiment of an instrument 22, 108 described above with reference to FIGS. 1 and 3, respectively. The dual-control surgical instrument 200 includes a parallel motion mechanism 204 with a tube 207 having joints at each end, coupled to a wrist joint 203, which is coupled to the end effector 202. In this embodiment, the end effector 202 includes jaws 205. In some aspects the parallel motion mechanism 204 and wrist joint 203 function such that the position of a reference frame at the distal end of the mechanism may be changed with respect to a reference frame at the proximal end of the mechanism without changing the orientation of the distal reference frame. Details of an applicable parallel motion assembly including related joints of an applicable instrument are further disclosed in U.S. patent application Ser. No. 11/762,165 filed Jun. 13, 2007, disclosing "Minimally Invasive Surgical System" and U.S. Pat. No. 7,942,868 filed Jun. 13, 2007, disclosing "Surgical Instrument with Parallel Motion Mechanism," which are incorporated by reference herein in their entirety.

Figure 6:
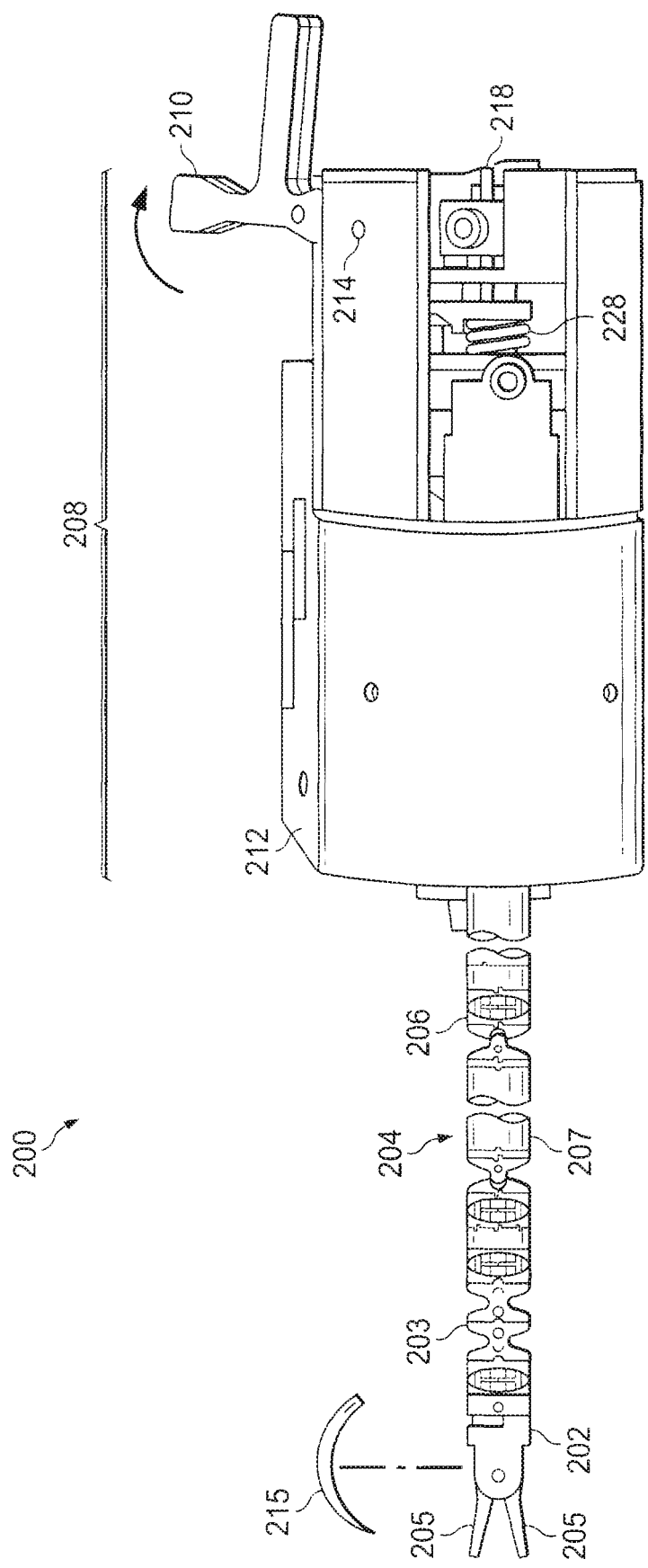
FIG. 6 illustrates a side view of the dual-control surgical instrument of FIG. 5 with the end effector in an open position according to one embodiment of the present disclosure.

The parallel motion mechanism 204 is coupled to a distal end of a shaft 206. The dual-control surgical instrument 200 further includes dual-control instrument activation system 208. The proximal end of the shaft 206 is coupled to a dual-control instrument activation system 208. The system 208 includes a lever 210 pivotally connected to a housing 212 by a pivot connector 214. In this embodiment, the dual-control instrument activation system 208 is operational to open and close the end effector 202 in response to pivotal movement of the lever 210. As shown in FIG. 6, the lever 210 is rotated (clockwise in this embodiment) about the pivot connector 214 to open the gripping end effector 202 to receive a surgical accessory such as a needle 215. The lever 210 is rotated in the opposite direction (counter-clockwise in this embodiment) to close the end effector 202 to firmly grasp the needle 215 within the jaws 205 of the end effector. The lever 210 may be manually operated by a user or may be manipulated by a teleoperated actuator as will be described below. In an alternative embodiment, the rotation of the lever may have the opposite influence on the rod (i.e. counter-clockwise rotation advances the rod and clockwise rotation retracts the rod). In various embodiments, the rod may be configured such that advancement may either open or close the end effector. Likewise, the retraction may either open or close the end effector.

Figure 7:
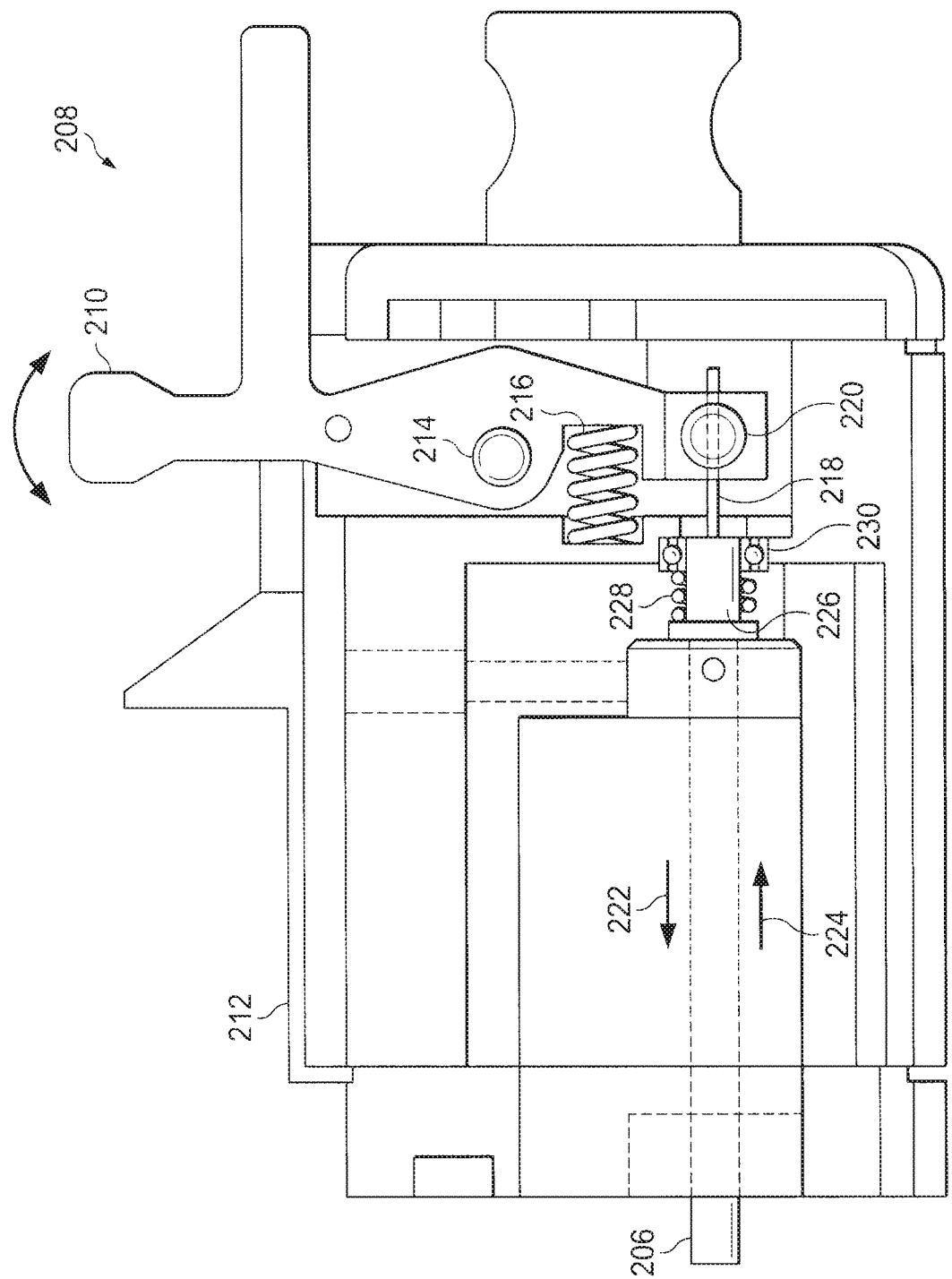
FIG. 7 is a partial cross-section view of the instrument of FIGS. 5 and 6.
Figure 8:
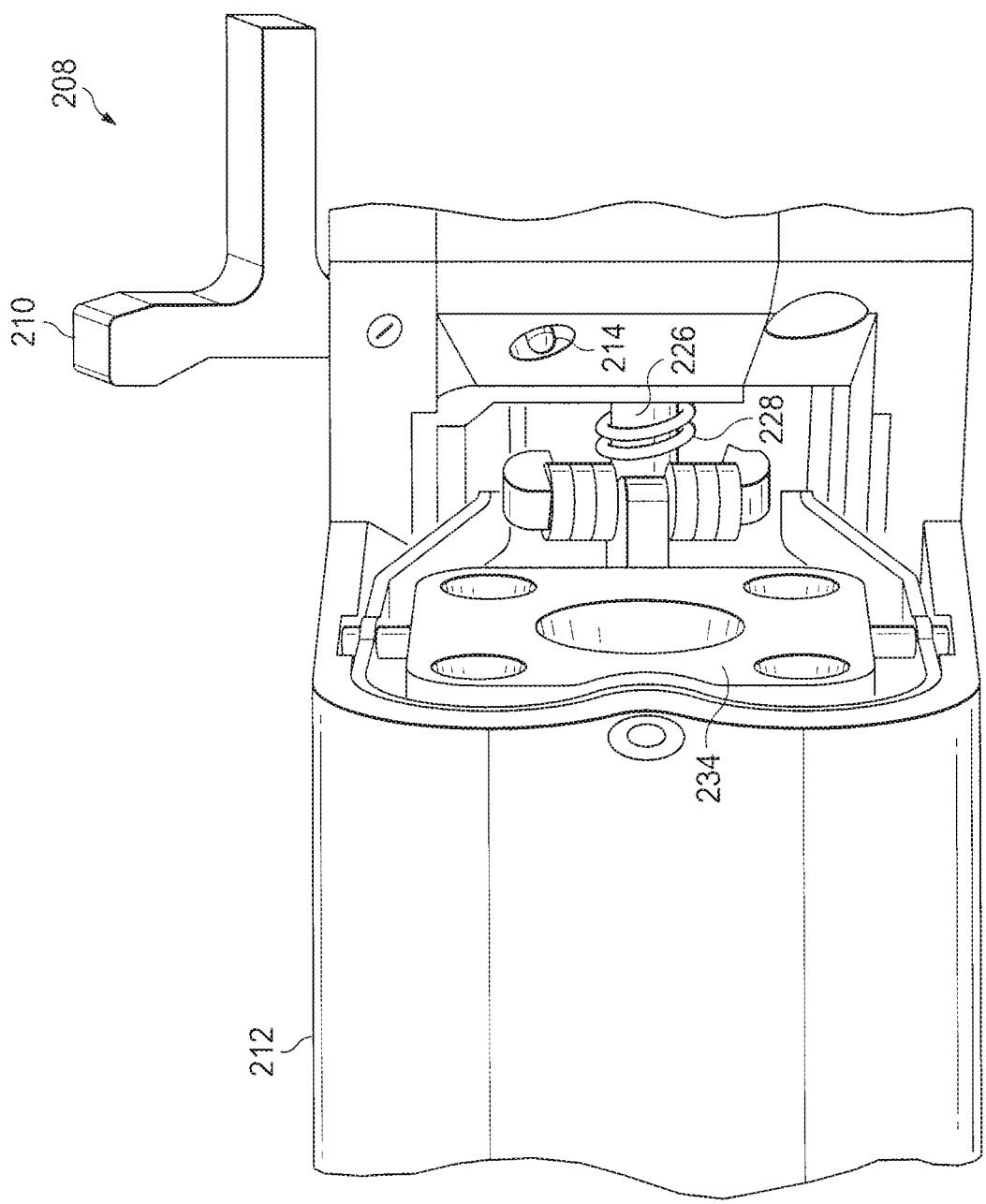
FIG. 8 is a partial internal view of the dual-control surgical instrument of FIGS. 5 and 6.

FIG. 7 is a partial cross-sectional view and FIG. 8 is a partial internal view of the dual-control instrument activation system 208. In these views, the lever 210 is biased toward the position shown in FIG. 5, in which the end effector 202 is closed. The lever 210 is biased by a spring 216, which in this embodiment is a coil spring. In alternative embodiments, other biasing elements, including other types of springs, elastomeric material components, or shape-memory material elements may be used. The lever 210 is coupled to a drive element 218 by a clamp 220. In this embodiment, the drive element is a single rod 218 which may be formed of nitinol, stainless steel, or another suitable medical-grade metal, ceramic, or polymer. Alternatively, the rod 218 may include more than one material. For example, a more flexible material may be used in areas that extend through the joints. In one embodiment, a distal portion of the rod may include a tungsten cable with an ETFE covering and a proximal portion formed of stainless steel. Optionally, an FEP covering may extend over all or a portion of the rod. The rod 218 may extend through the housing 212 and through the shaft 206 to couple with the end effector 202. The clamp 220 grips the rod 218 and can rotate within the lever 210 to avoid excess bending of the rod. In this embodiment, clockwise rotation of the lever 210 compresses the spring 216 and advances the rod 218 linearly in the direction 222 to open the jaws of the end effector 202. Counter-clockwise rotation of the lever 210 retracts the rod 218 linearly in the direction 224 to close the jaws of the end effector 202. The bias of the spring 216 may be sufficiently strong that the rod 218 will be biased to return to the closed position if the lever is not held in the open position by an outside force. In alternative embodiments, the dual-control instrument activation system may bias the end effector to an open position.

The 208 further includes a driver holder 226 and a spring 228 which applies gentle axial compression on the driver holder 226. A cylindrical bearing 230 holds the spring 228 in place within the housing 212. The activation system 208 further includes gimbal assemblies (e.g., 234 in FIG. 8, others not shown) and other mechanisms which operate cables, rods or other drive mechanisms (not shown) to actuate the roll, parallel motion, and wrist joint components through the translation of pitch, yaw, and roll movements. Further aspects of the gimbal assemblies for use in teleoperated surgical activation systems may be found in U.S. patent application Ser. No. 12/060,104 filed Mar. 31, 2008, disclosing "Coupler to Transfer Controller Motion from a Robotic Activation system to an Attached Instrument;" U.S. patent application Ser. No. 11/762,165 filed Jun. 13, 2007, disclosing "Minimally Invasive Surgical System;" and U.S. patent application Ser. No. 12/780,758 filed May 14, 2010, disclosing "Force Transmission for Robotic Surgical Instrument," which are incorporated by reference herein in their entirety. Some gimbal assemblies may be horizontally arranged gimbal assemblies that function to translate or copy inputs from one gimbal assembly to another horizontally aligned gimbal assembly via a translation components. Translation components may include gears, levers, cables, pulleys, cable guides or other components to transfer or copy the mechanical motion between gimbal assemblies. Other gimbal assemblies may be vertically arranged gimbal assemblies that function to translate inputs from one gimbal assembly to another vertically aligned gimbal assembly. Translation components such as those described above may be used to transfer the mechanical motion between vertically arranged gimbal assemblies.

In this embodiment, the drive rod 218 that actuates the grasping action of the end effector 202 passes through a central opening in vertically aligned gimbal assemblies. In alternative embodiments, the drive element 218 may be a pair of cables, where one is pulled to open the jaws of the end effector and one is pulled to close the jaws of the end effector. In some embodiments, the gripping drive element 218 may be a multi-component drive element with, for example, a rigid or semi-rigid rod at the proximal end near the lever and a more flexible component at the distal end where the drive element passes through the parallel motion mechanism and wrist joints. The flexible component of the rod may be a thin wire (e.g., nitinol), a coated or uncoated cable, or a pair of coated cables that cooperate together. As the flexible component passes through the parallel motion mechanism and/or the wrist joints, a sheath may be used to prevent buckling. Alternatively, the flexible components may be guided by the inner diameters of the parallel motion mechanism and/or wrist joints.

Figure 9:
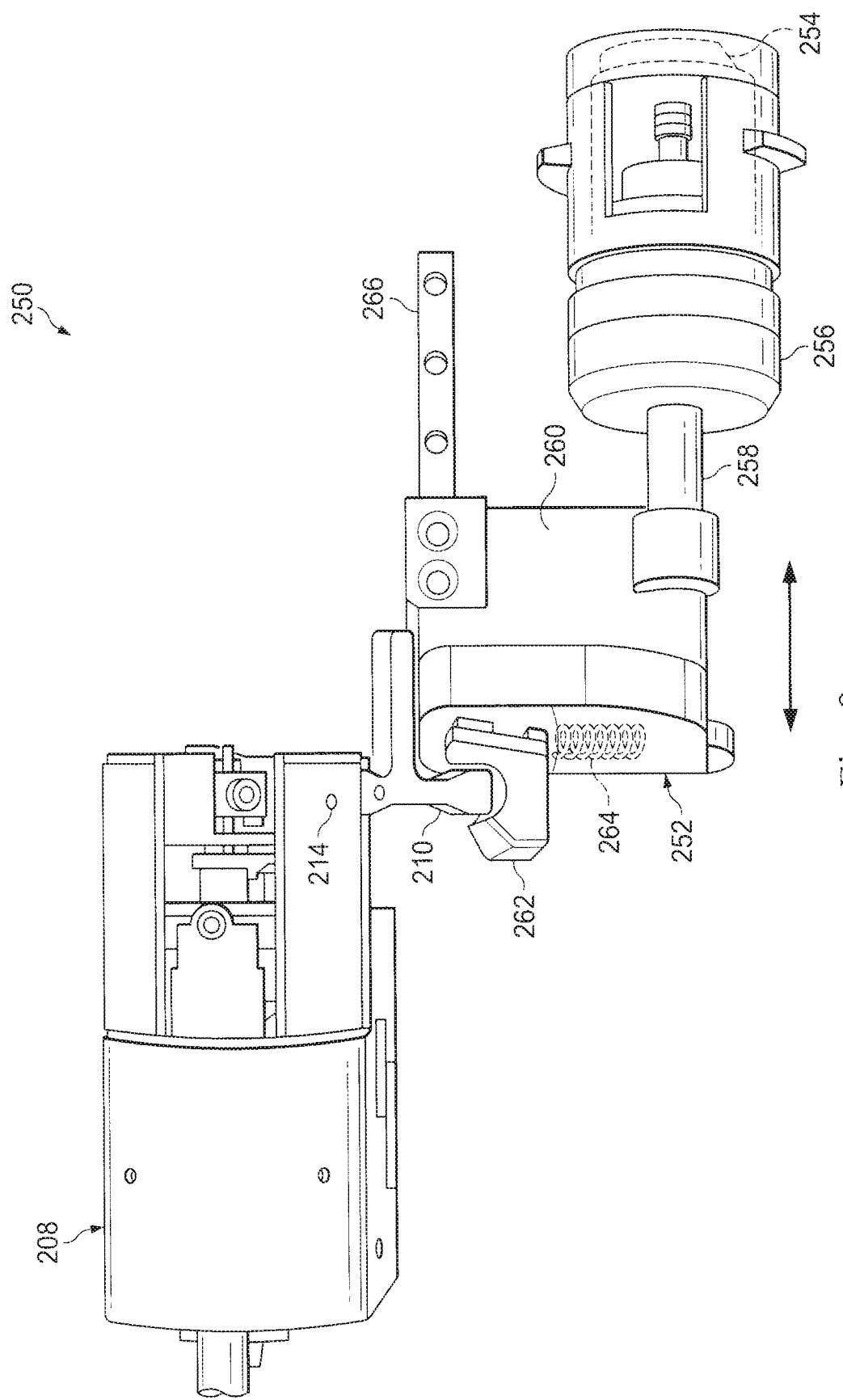
FIG. 9 is a partial side view of the dual-control surgical instrument of FIGS. 5 and 6 coupled to a grip actuator.

As shown in FIG. 9, the dual-control instrument activation system 208 can be a component of an instrument operation system 250. The instrument operation system 250 also includes a grip actuator 252 which couples to and moves the lever 210 about the pivot connector 214. The grip actuator include rotary and/or linear motion encoders 254. One or more motors 256, such as servomotors, drive an associated ball screw 258, which moves an actuator housing 260 linearly forward or backward along a path generally parallel to the axis of the ball screw 258. A lever capture mechanism 262, which in this embodiment has a hook shape, is sized to receive and couple with an end portion of the lever 210. In alternative embodiments, the capture mechanism may be a socket, a clamp, or other mechanism configured to hold and move the lever 210. A bias component 264, such as a spring, is housed within the actuator housing 260 and exerts a biasing force that presses the lever capture mechanism 262 toward the lever 210. A support slide 266 provides linear support to the grip actuator 252.

Figure 10:
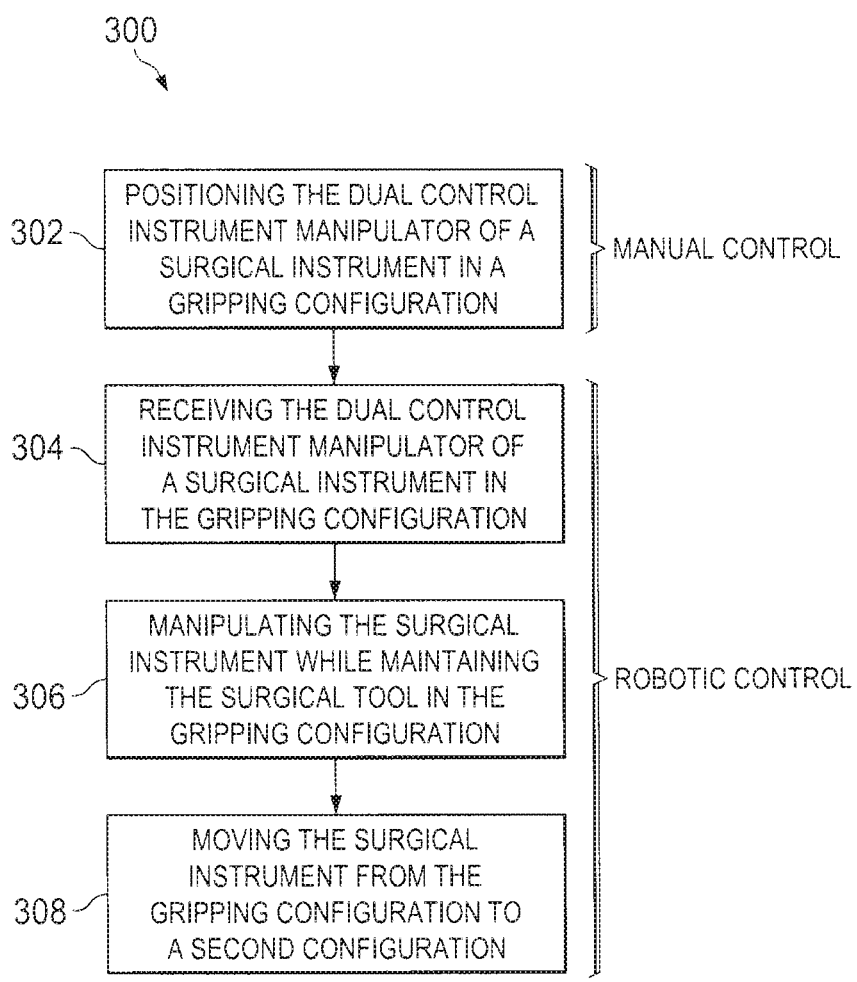
FIG. 10 is a flow chart illustrating a method of operating a dual-control surgical instrument according to another embodiment of the present disclosure.

The surgical instrument 200 may be used for minimally invasive teleoperated surgery performed through multiple surgical incisions or through a single incision. As shown in FIG. 10, a flow chart 300 illustrates a method of operating the surgical instrument 200. During the course of a teleoperational surgical procedure, a surgeon may desire to introduce a surgical accessory such as a needle, gauze, a sponge, a clamp, or other useful accessory into the surgical site. At step 302, a user, such as a surgical assistant, grasps the surgical accessory 215 within the jaws of the end effector 202 by moving the lever 210 about the pivot connector 214 to compress the spring 216. The movement of the lever 210 advances the rod 218, causing the jaws of the end effector 202 to open. The surgical assistant then places the surgical accessory 215 between the jaws of the end effector 202. The surgical assistant releases the lever 210, allowing the lever to return to a prebiased position corresponding to a closed position of the end effector 202. A closed position includes the configurations of the end effector 202 in which the jaws 205 are closed onto or around the surgical accessory or are in closed contact with each other. The surgical instrument 200 is now in a prearranged gripping configuration with the surgical accessory gripped between the jaws of the end effector 202.

At step 304, the surgical assistant couples the surgical instrument 200 to the grip actuator 252. More specifically, the grip actuator 252 receives the end of the lever 210 in the lever capture mechanism 262. The instrument 200 remains in the closed gripping configuration while the end effector 202 and the gripped surgical accessory 216 are introduced into the surgical site. The introduction of the instrument 200 and the surgical accessory 215 may be through a cannula and/or other types of access ports leading into the surgical site in the patient.

At step 306, the surgical instrument 200 is moved by the operation system 250 while the instrument continues to grip the surgical accessory 215. One or more control signals are generated by and sent from the computer system 18 to instruct the operation system to maintain the surgical instrument in the gripping configuration. While the grip is maintained, the parallel motion mechanism 204 or the wrist joint 203 may be moved, causing the gripped surgical accessory 215 to be moved into position within the surgical site. To release or readjust the surgical accessory 215, at step 308, the instrument is moved from the closed gripping configuration to a release or loosened grip configuration. One or more control signals are generated by and sent from the computer system 18 to instruct the operation system to move from the closed gripping configuration to an open or loosened configuration. More specifically, the grip actuator 252 moves the lever capture mechanism 262, causing the captured lever 210 to pivot about the pivot connector 214 to open or loosen the jaws of the end effector 202.

In an alternative embodiment, the surgical accessory may be a device that should be introduced into the surgical site in a held-open configuration. For example, a surgical clip may need to be held open until it surrounds a blood vessel to be occluded. In this embodiment, an instrument that includes a clip applier may be introduced with the clip applier held in an open position. A user may manually manipulate the dual-control activation system to grip the clip applier and an attached surgical clip in an open gripping position. The dual-control activation system may be transferred to the control of the instrument operation system with the dual-control activation system continuing to be held in the open gripping position. The dual-control activation system may be biased toward an open position. Alternatively, the dual-control activation system may be biased toward a closed position with the operator and teleoperated forces applied to maintain the instrument in the open position against the bias.

In still another alternative, the dual-control activation system may be actuated manually even after it is attached to the teleoperated instrument operation system. Such an embodiment may be used, for example, to deliver a manual force more powerful than can be delivered by the motors of the PSC. One such example of a manual override may be for a large stapler that requires a short burst of force that may be most efficiently provided with manual actuation rather than with teleoperated actuation.

Figure 11:
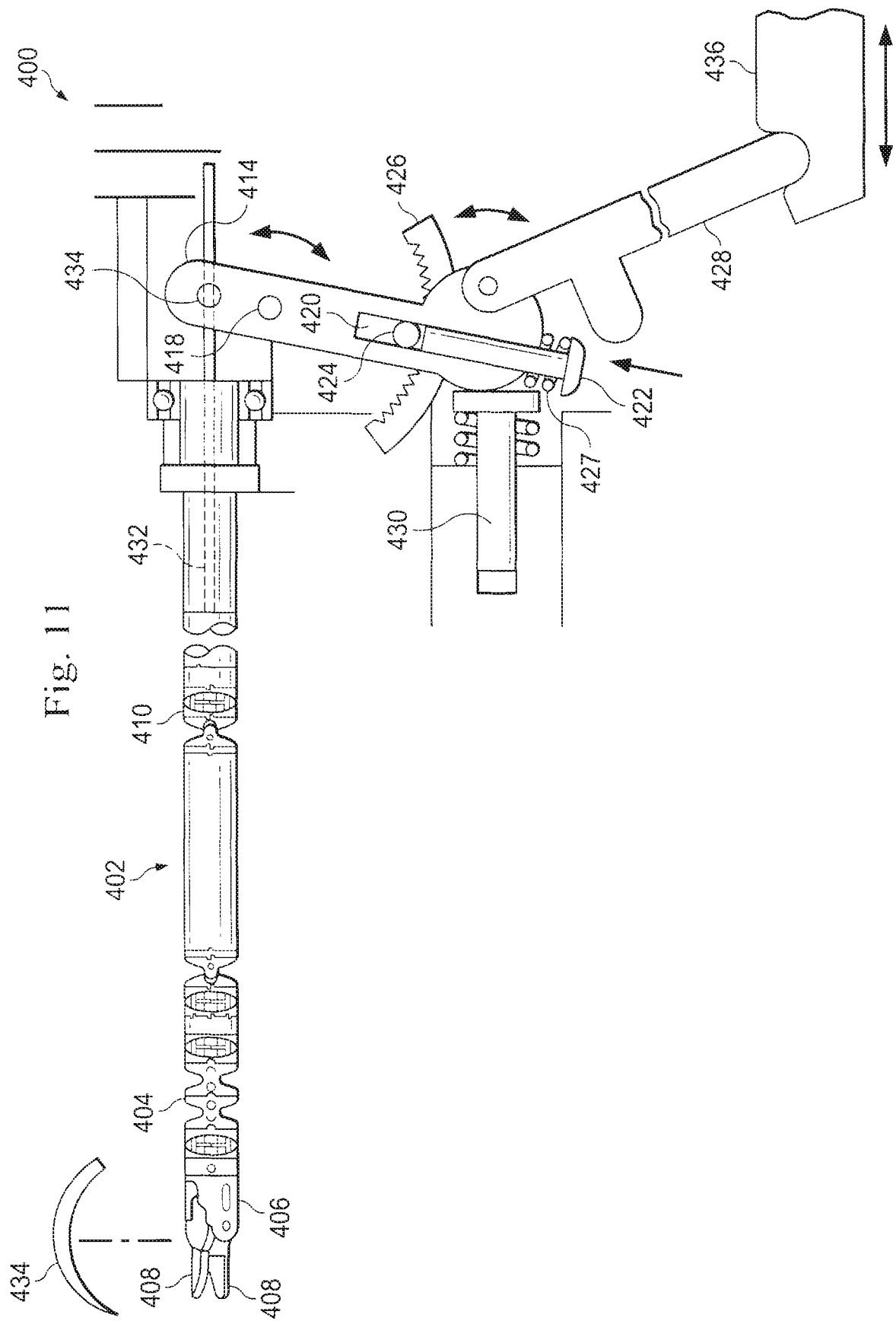
FIG. 11 illustrates a partial side view of a dual-control surgical instrument according to another embodiment of the present disclosure.

FIG. 11 illustrates a partial side view of a dual-control surgical instrument 400 according to another embodiment of the present disclosure. Instrument 400 is an illustrative embodiment of an instrument 22, 108 described above with reference to FIGS. 1 and 3, respectively. The dual-control surgical instrument 400 includes a parallel motion mechanism 402, coupled to a wrist joint 404, which is coupled to an end effector 406. In this embodiment, the end effector 406 includes jaws 408. The parallel motion mechanism 402 is coupled to a distal end of a shaft 410. The proximal end of the shaft 410 is coupled to an actuator 414 which is pivotally connected to a housing (not shown) by a pivot connector 418. The actuator 414 includes an elongated slot 420 sized to receive an elongated portion of a ratchet button 422. A ratchet pin 424 is coupled to or integrally formed at a distal end of the ratchet button 422. A toothed ratchet arm 426 is coupled to the housing. The teeth of the ratchet arm 426 are sized to receive the ratchet pin 424 therebetween. A spring 427 extends between the ratchet button 422 and the actuator 414. A lever 428 is pivotally connected to the actuator 414. Alternatively the lever 428 could be connected to the housing. A drive member 432, which in this embodiment is a rod, is clamped to the actuator 414 by a clamp 434.

In one example of use, the ratchet button 422 is depressed (for example, manually) causing the pin 424 to move from between a pair of teeth of the ratchet arm 426. The actuator 414 is pivoted clockwise about the pivot connector 418 and the rod 432 is retracted, moving the jaws 408 to a closed configuration. With the button 422 released and the spring 427 relaxed, the pin 424 is biased into engagement with the ratchet arm 426 and the rod 432 is locked in position with the jaws 408 in the closed configuration.

The movement of the rod 432 may be transferred to teleoperated instrument control while maintaining the jaws 408 in the closed and locked position. For example, an instrument activation system (manual or teleoperated) including a biasing member 430 (e.g., a spring-loaded plunger) and a grip actuator 436 may be used to control the instrument 400. The lever 428 is engaged by the grip actuator 436 and is pivoted clockwise while the biasing member 430 provides a reaction force against the movement of the actuator 414. The clockwise motion of the lever 428 eventually engages and depresses the button 422, releasing the pin 424 from the ratchet arm 426, thus allowing the further movement of the 436 to rotate the actuator 414 about the pivot connector 418 either clockwise to retract the rod 432 to close the jaws 408 or counter-clockwise to advance the rod and open the jaws. The biasing member 430 biases the actuator 414 to an advanced position in which the jaws 408 are open.

Figure 12:
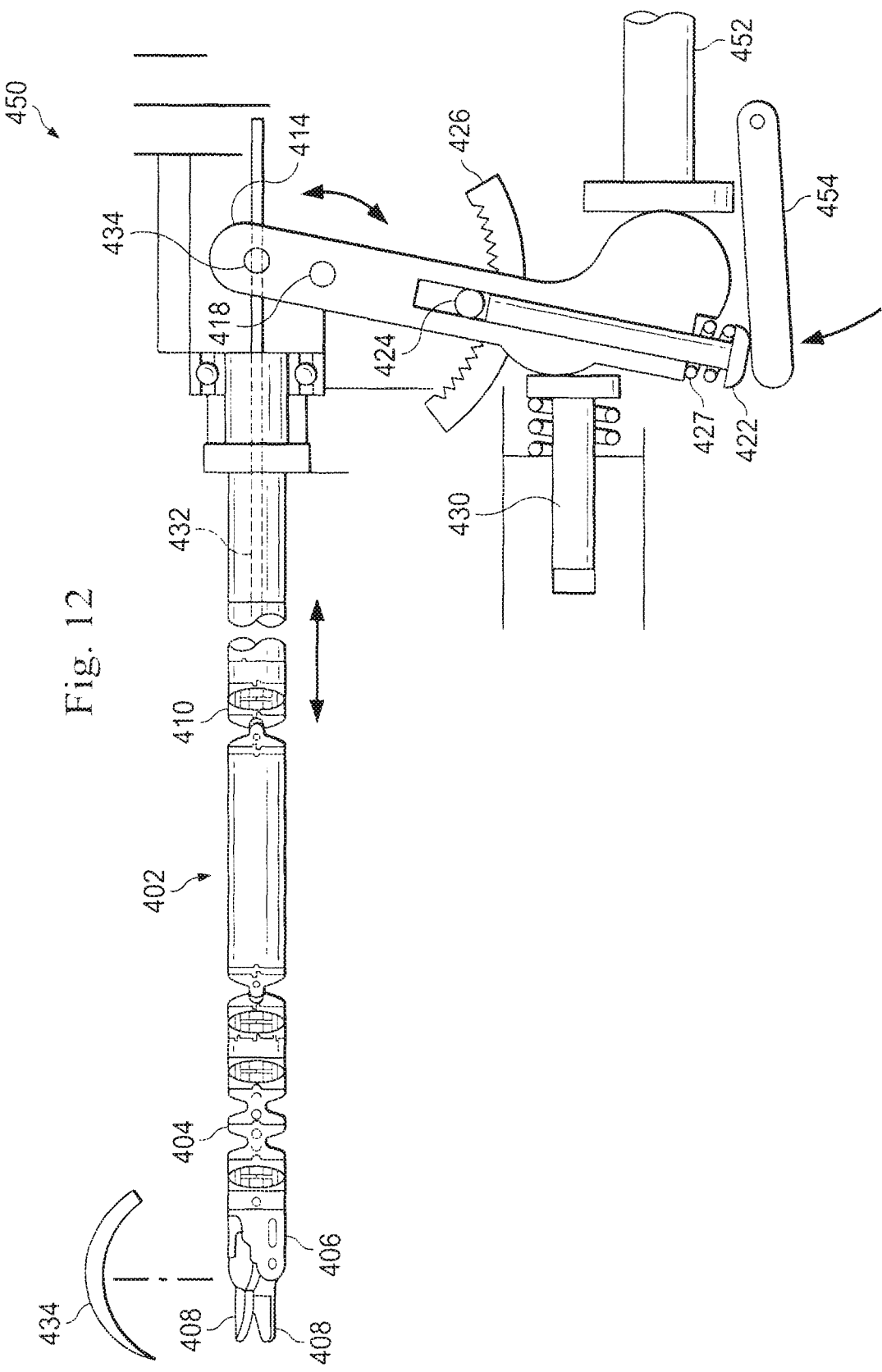
FIG. 12 illustrates a partial side view of a dual-control surgical instrument according to another embodiment of the present disclosure.

FIG. 12 illustrates a partial side view of a dual-control surgical instrument 450 according to another embodiment of the present disclosure. The surgical instrument 450 is similar to the instrument 400 of FIG. 400 and similar components will retain the same reference numerals. In this embodiment, an actuation component 452 provides a force on the actuator 414 and an actuation component 454 provides a force on the button 422. The actuation components 452, 454 may be separate actuation components or may be part of a common actuation component. When the actuation component 454 depresses the button 422 to release the pin 424 from the ratchet arm 42 and the activation system 452 exerts a force on the actuator 414, the actuator 414 moves clockwise and depresses the bias member 430. The actuator 414 thus retracts the rod 432 and the jaws 408 are closed. When the force provided by the activation system 452 is withdrawn or lessened while the pin 424 is disengaged from the ratchet arm 426, the bias member 430 moves the actuator counter-clockwise, and the rod 432 is advanced, opening the jaws 408. In the embodiment of FIG. 12, the surgical instrument 450 may be locked and unlocked, repeatedly, by the activation system 454 using a dedicated actuator (e.g., a motor or solenoid). In FIG. 11, when the instrument 400 is unlocked by lever 428, it remains unlocked.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A surgical system comprising:
   an instrument and a teleoperated instrument operation system;
   wherein the instrument comprises a drive member having a proximal end and a distal end, an end effector coupled to the distal end of the drive member, a ratchet assembly coupled to the proximal end of the drive member, and a lever pivotally coupled to the ratchet assembly;
   wherein the ratchet assembly includes a pin, a gear, a spring-loaded button, and a spring in the spring-loaded button;
   wherein the lever is configured to pivot relative to the ratchet assembly to engage the spring-loaded button, which compresses the spring in the spring-loaded button to disengage the pin from the gear;
   wherein the lever in a first position places the ratchet assembly in a gripping position in which the end effector grips a surgical accessory;
   wherein the lever in a second position places the ratchet assembly in a release position in which the end effector releases the gripped surgical accessory;
   wherein the lever is movable from the first position to the second position while the lever compresses the spring in the spring-loaded button; and
   wherein the teleoperated instrument operation system comprises a capture mechanism configured to move the lever between the first and second positions.

2. The surgical system of claim 1:
   wherein the drive member comprises a rod coupled between the end effector and the ratchet assembly.

3. The surgical system of claim 1:
   wherein the teleoperated instrument operation system comprises a servomotor operably coupled to the capture mechanism.

4. The surgical system of claim 1:
   wherein the lever is adapted to move the ratchet assembly between a plurality of gripping positions between the first and second positions; and
   wherein each of the plurality of gripping positions corresponds to a different grip arrangement of the end effector.

5. The surgical system of claim 1:
   wherein the spring-loaded button is accessible for manual engagement by an operator.

6. The surgical system of claim 1:
   wherein the ratchet assembly comprises an actuator coupled to the proximal end of the drive member; and
   wherein the actuator is configured for pivotal motion relative to the gear when the lever moves between the first and second positions.

7. The surgical system of claim 6:
   wherein the actuator comprises a slot housing both the pin and an elongated portion of the button.

8. The surgical system of claim 1 further comprising:
   a biasing member engaged with the ratchet assembly;
   wherein the biasing member provides a force biasing the ratchet to the gripping position.

9. A surgical system comprising:
   an instrument and a teleoperated instrument operation system;
   wherein the instrument comprises a drive member having a proximal end and a distal end, an end effector coupled to the distal end of the drive member, a ratchet assembly coupled to the proximal end of the drive member, and a lever pivotally coupled to and pivotable relative to the ratchet assembly;
   wherein the ratchet assembly comprises a release mechanism;
   wherein the release mechanism comprises a spring-loaded button;
   wherein the lever in a first position places the ratchet assembly in a gripping position in which the end effector grips a surgical accessory;
   wherein the lever in a second position actuates the spring-loaded button to place the ratchet assembly in a release position in which the end effector releases the gripped surgical accessory; and
   wherein the teleoperated instrument operation system comprises a capture mechanism configured to move the lever between the first and second positions.

* * * * *